US006824768B2

(12) United States Patent
Stalgis et al.

(10) Patent No.: US 6,824,768 B2
(45) Date of Patent: Nov. 30, 2004

(54) RIBAVIRIN-PEGYLATED INTERFERON ALFA INDUCTION HCV COMBINATION THERAPY

(75) Inventors: Carlos O. Stalgis, Millington, NJ (US); Janice K. Albrecht, Winter Park, FL (US); Paul W. Glue, Flemington, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/464,426

(22) Filed: Dec. 16, 1999

(65) Prior Publication Data

US 2002/0119122 A1 Aug. 29, 2002

Related U.S. Application Data

(60) Provisional application No. 60/112,773, filed on Dec. 18, 1998.

(51) Int. Cl.[7] ........................ A61K 38/21; A61K 39/00; A61K 39/29; A61K 31/70; C07K 38/21
(52) U.S. Cl. ................ 424/85.7; 424/184.1; 424/228.1; 514/43; 530/351
(58) Field of Search ............................ 424/85.7, 184.1, 424/228.1, 85.4, 189.1, 281.1; 514/43; 530/351; 435/5, 6; 536/23.1, 23.52, 24.3

(56) References Cited

U.S. PATENT DOCUMENTS

| 5,503,828 A | | 4/1996 | Testa et al. | |
|---|---|---|---|---|
| 6,172,046 B1 | * | 1/2001 | Albrecht | ...................... 514/43 |
| 6,472,373 B1 | * | 10/2002 | Albrecht | ...................... 514/43 |

FOREIGN PATENT DOCUMENTS

| EP | 0 707 855 A2 | * | 4/1996 |
|---|---|---|---|
| WO | WO 95/13090 | * | 5/1995 |

OTHER PUBLICATIONS

Chemello et al. 1994. Response to ribavirin and to a combination of both in patients with chronic hepatitis C and its relation to HCV genotypes. Journal of Hepatology. vol. 21. (Suppl. 1), p. S12. Abstract No. GS 5/29.*
Xu et al. 1998. PK/PD modeling approach to support clinical development of a long–acting interferon (RO25–3036) for the treatment of chronic hepatitis C. Clin. Pharmacol. Ther. vol. 63. No. 2, p. 162. Abstract No. Pl–101.*
Lai, et al., *Gastroenterology*, Nov. 1996, vol. III, pp. 1307–1312.
Sato, et al., NS5A Region and the Prediction of Interferon Effect, Igaku–no–Ayumi (May 3, 1997), vol. 181, (No. 5) pp. 330–340 (Translation).
Hayashi, N., *Today's Therapy*, Chronic Hepatitis, Konnichi--no–Chiryo–Sisin, Jan. 15, 1997, p. 403 (Translation).

Gunther, R., "What is Ribavirin?" and "Combination with Ribavirin for Non–Responders", Medical Tribune, Nr 22, May 30, 1997, www.hepatitis–c.de/wasriba.htm (in German).
Schalm, SW., et al., Digestive Diseases and Sciences, vol. 41, (No. 12) Dec. 1996, Supplement, pp. 131S to 134S.
Reichard, O.., et al., "Interferon–Alpha and Ribavirin versus Interferon alpha as Therapy for Chronic Hepatitis C—A randomized Double–blind placebo–controlled study." American Association for the Study of Liver Diseases, 1996 Annual Meeting, www.hepatitis–c.de/riba.htm.
Pol, S., et al., "Ribavirin–Interferon v. Interferon alone in Non–Responders to IFN in Chronic Hepatitis C", American Association for the Study of Liver Diseases, 1996 Annual Meeting,. www.hepatitis–c.de/riba.htm.
Lurie, Y., et al., "Ribavirin Interferon Combination for chronic HCV", American Gastroenterology Association Digestive Disease Week meeting in Washington, May 1997, www.hepatitis–c.de/riba.htm.
Bellobuono, A., et al. "Ribavirin and interferon–alph combination therapy v. interferon–alpha alone in the treatment of chronic hepatitis C; A randomized clinical trial;" Journal of Viral Hepat 1997; vol. 4, 185–191.
Weiland, et al., "Combination Treatment with Interferon Alpha–2b and Ribavirin in Patients Suffering from Chronic Hepatitis C Relapsing After, or Not Responding to Earlier Treatment with Interferon," Translation of Abstract from Lakarstamman (Swedish Physicians' Meeting) Stockholm—Dec. 1993.
El Zayadi, et al., "Combination treatment of alpha interferon–2b and ribavirin in chronic hepatitis C genotype"< Hepatology 22 (4 Pt 2),152A (1995).
Bizollon, et al., "Ribavirin and interferon treatment for Hepatitis C recurrence [sic] Following Orthotopic Liver Transplantation", Abstract, *Hepatology* 21 Suppl 1, p. S58 (1994).

* cited by examiner

*Primary Examiner*—Shanon Foley
(74) *Attorney, Agent, or Firm*—Thomas D. Hoffman; Sandy Zaradic

(57) ABSTRACT

There is disclosed a method for treating antiviral treatment naives patient having chronic hepatitis C infection to eradicate detectable HCV-RNA involving a combination therapy using (1) a therapeutically effective inducing amount of ribavirin and a therapeutically effective induction dosing amount of pegylated interferon-alfa, e.g, pegylated interferon-alfa-2b for a first treatment time period sufficient to substantially lower detectable HCV-RNA, followed by (2) administering a therapeutically effective amount of ribavirin and an therapeutically effective amount of pegylated interferon-alfa, e.g., pegylated interferon alfa-2b for a second treatment time period sufficient to eradicate detectable HCV-RNA at least by end of the second treatment time period and to maintain no detectable HCV-RNA for at least 24 weeks after the end of the second treatment time period.

15 Claims, No Drawings

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:

```
            (A) LENGTH: 22 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 1:

GTGGTCTGCG GAACCGGTGA GT                                              22

(2) INFORMATION FOR SEQ ID NO: 2:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 2:

TGCACGGTCT ACGAGACCTC                                                 20

(2) INFORMATION FOR SEQ ID NO: 3:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 3:

CTGTGAGGAA CTACTGTCTT C                                               21

(2) INFORMATION FOR SEQ ID NO: 4:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 4:

CCCTATCAGG CAGTACCACA A                                               21
```

RIBAVIRIN-PEGYLATED INTERFERON ALFA INDUCTION HCV COMBINATION THERAPY

CROSS-REFERENCE TO RELATED APPLICATION

This application claims the benefit under 35 U.S.C. §119 (e) of U.S. Provisional Application Ser. No. 60/112,773, filed Dec. 18, 1998.

BACKGROUND OF THE INVENTION

The present invention relates to methods of treating patients having chronic hepatitis C infection by administering a therapeutically effective induction amount of ribavirin and a therapeutically effective induction amount of pegylated interferon-alfa for a first treatment time period sufficient to substantially lower detectable HCV-RNA, followed by (2) administering a therapeutically effective amount of ribavirin and an therapeutically effective amount of pegylated interferon-alfa for a second treatment time period sufficient to eradicate detectable HCV-RNA at least by the end of the second treatment time period and to maintain no detectable HCV-RNA for at least 24 weeks after the end of the second treatment time period.

Chronic infection with hepatitis C virus is an insidious and slow-progressing disease having a significant impact on the quality of life. It can eventually result in cirrhosis of the liver, decompensated liver disease and/or hepatocelluar carcinoma.

International Publication No. WO98/48840 discloses use of pegylated interferon alfa to treat hepatitis C infections.

Nieforth et al. (Clin. Pharmacol. Ther., 1996, 59:636–646) has reported a comparison of the in vivo activity of Roferon®A and a polyethylene glycol-modified Roferon® A in healthy volunteers. The results, however, suggested that the conjugates could not be administered less than twice weekly and therefore offered little therapeutic advantage over the unmodified counterpart.

Co-pending, commonly assigned U.S. patent application Ser. No. 08/742,305 discloses methods of administering polymer-cytokine conjugates to individuals susceptible to treatment with the cytokine, but does not disclose the method of this invention.

Polyethylene glycol modification of other proteins has been reported by Fuertges et al. (Journal of Controlled Release,1990, Vol.11:139–48).

Combination therapy of interferon alfa-2b and ribavirin to treat chronic hepatitis C for 24 weeks is disclosed by Reichard et al. (Lancet 1998; 351;83–87)

T. Poynard et al. (Lancet, 1998, Vol. 352, 1426–1432) disclose that treating chronic hepatitis C patients who had not been treated with interferon or ribavirin with 3 MIU of interferon alfa-2b TIW plus 1000–1200 mg of ribavirin per day for 48 weeks resulted in a sustained virological response at 24 weeks after treatment in 43% of the patients. See also J. G. McHutchinson et al. (N. Engl. J. Med., 1998, 339:1485–1492), G. L. Davis et al. (N. Engl. J. Med. 339:1493–1499) disclose that treating chronic hepatitis C patients who relapsed after treatment with interferon with 3 MIU of interferon alfa 2b Tim plus 100–1200 mg of ribavirin per day for 48 weeks results in higher rates of sustained virologic response than treatment with interferon alone.

There is a need to provide an improved therapy for treating chronic hepatitis C patients to produce a sustained virological response at 24 weeks after treatment in a greater number of patients.

SUMMARY OF THE INVENTION

The present invention provides a method of treating patients having chronic hepatitis C infections which comprises (1) administering a therapeutically effective induction dosing amount of ribavirin and an therapeutically effective induction dosing amount of pegylated interferon-alfa for a first treatment time period sufficient to substantially lower detectable HCV-RNA, followed by (2) administering a therapeutically effective amount of ribavirin and an therapeutically effective amount of pegylated interferon-alfa for a second treatment time period sufficient to eradicate detectable HCV-RNA at least by the end of the second treatment time period and to maintain no detectable HCV-RNA for at least 24 weeks after the end of the second treatment time period.

The present invention also provides a method of treating patients having chronic hepatitis C infections which comprises (1) administering, in a first treatment time period of at least about four weeks, about 400–1200 mg per day of ribavirin and about 1.5 micrograms per kilogram of pegylated interferon-alfa-2b twice a week, followed by (2) administering, in a second treatment time period of up to about forty-four weeks, about 800–1200 mg per day of ribavirin and about 0.5 to 1.5 micrograms per kilogram of pegylated interferon-alfa-2b once a week.

The present invention also provides a method method of treating patients having chronic hepatitis C infections which comprises (1) administering, in a first treatment time period of from about four weeks up to about twelve weeks, about 400–1200 mg per day of ribavirin and about 1.5 micrograms/kilogram of pegylated interferon-alfa-2b twice a week followed by (2) administering, in a second time of from about thirty-six to about forty-four weeks, period about 800–1200 mg per day of ribavirin and about 0.5 to about 1.5 micrograms per kilogram of pegylated interferon-alfa-2b once a week basis.

The present invention also provides a method method of treating patients having chronic hepatitis C infections which comprises (1) administering, in a first treatment time period of about four weeks, about 800–1200 mg per day of ribavirin and about 1.5 micrograms/kilogram of pegylated interferon-alfa-2b twice a week, followed by (2) administering, in a second time of about forty-four weeks, about 800–1200 mg per day of ribavirin and about 1.5 micrograms/kilogram of pegylated interferon-alfa2b once a week

DETAILED DESCRIPTION

The present method of treating patients having chronic hepatitis C infections comprises two treatment time periods. In the first treatment time period, a therapeutically effective induction dosing amount of ribavirin and an therapeutically effective induction dosing amount of pegylated interferon-alfa is administered for a first treatment time period sufficient to substantially lower detectable HCV-RNA serum levels, preferably by a power of 10, more preferably by at least two powers of ten, i.e., at least $10^2$, lower than the initial HCV-RNA serum level. In a preferred embodiment of the present invention, the HCV-RNA is eradicated (i.e., lowered to less than 100 copies/mL) during the first treatment time period. In the second treatment time period, the method entails administering a therapeutically effective amount of ribavirin and an therapeutically effective amount of pegylated interferon-alfa long enough to eradicate detectable HCV-RNA at least by the end of the second treatment time period and to maintain no detectable HCV-RNA for at least 24 weeks after the end of the second treatment time period. In a preferred embodiment of the present invention, the HCV-RNA is eradicated (i.e., lowered to less than 100 copies/mL) during the second treatment time period and more preferably by the end of the first treatment time period; in this preferred embodiment the no detectable HCV-RNA level is maintained during the second treatment time period. The sum of the first and second treatment time periods is about 40–50 weeks preferrably 48 weeks.

The amount of ribavirin administered in the first treatment time period is from 400 to 1600 mg per day, preferably 600 to 1200 mg/day or about 800 to 1200 mg day and most preferably about 1000 to 1200 mg/kg a day. The amount of ribavirin administered in the second treatment time period is in the range of from about 800 to 1200 mg per day, preferably from about 1000 to 1200 mg per day.

The following preferred embodiments for administering pegylated interferon alfa are presented.

When the pegylated interferon-alfa administered is a pegylated interferon alfa-2b, the induction dosing amount of pegylated interferon alfa-2b administered in first treatment time period is in the range of 0.5 to 1.5 micrograms per kilogram twice a week (BIW) for at least four up to twelve weeks, and the amount of pegylated interferon alfa-2b administered in the second treatment time period is in the range of 0.5 to 1.5 micrograms per kilogram once a week (QW) for thirty-six up to to forty-four weeks.

When the pegylated interferon-alfa administered is a pegylated interferon alfa-2b, the induction dosing amount of pegylated interferon alfa-2b administered in first treatment time period is in the range of 0.5 to 1.5 micrograms per kilogram twice a week (BIW) for twelve weeks, and the amount of pegylated interferon alfa-2b administered in the second treatment time period is in the range of 0.5 to 1.5 micrograms per kilogram once a week (QW) for thirty-six weeks.

When the pegylated interferon-alfa administered is a pegylated interferon alfa-2b, the induction dosing amount of pegylated interferon alfa-2b administered in first treatment time period of five weeks is in the range of 0.5 to 1.5 micrograms per kilogram BIW (preferably 1.5 microgram per kilograms BIW) for one week, followed by 0.5 to 1.0 micrograms per kilogram BIW (preferably 1.0 micrograms per kilogram BIW) for four weeks, and the amount of pegylated interferon alfa-2b administered in the second treatment time period of forty-three weeks is in the range of 0.5 to 1.5 micrograms per kilogram once a week, prefrably 0.5 to 1.0 micrograms per kilogram once a week.

When the pegylated interferon-alfa administered is a pegylated interferon alfa-2b, the induction dosing amount of pegylated interferon alfa-2b administered in first treatment time period is in the range of 1.5 microgram per kilogram BIW for four weeks, and the amount of pegylated interferon alfa-2b administered in the second treatment time period is in the range of 0.5 micrograms per kilogram once a week for to forty-four weeks.

When the pegylated interferon-alfa administered is a pegylated interferon alfa-2b, the induction dosing amount of pegylated interferon alfa-2b administered in first treatment time period of five weeks is in the range of 1.5 micrograms per kilogram BIW for one week, followed by 1.0 micrograms per kilogram BIW for four weeks, and the amount of pegylated interferon alfa-2b administered in the second treatment time period of forty-three weeks is in the range of 0.5 to 1.0 micrograms per kilogram once a week.

When the pegylated interferon-alfa administered is a pegylated interferon alfa-2b, the induction dosing amount of pegylated interferon alfa-2b administered in first treatment time period is 1.5 micrograms per kilogram BIW for twelve weeks, and the amount of pegylated interferon alfa-2b administered in the second treatment time period is in the range 1.0 micrograms per kilogram once a week for thirty-six weeks.

When the pegylated interferon-alfa administered is a pegylated interferon alfa-2a, the induction dosing amount of pegylated interferon alfa-2a administered in first treatment time period is in the range of 20 to 250 micrograms BIW, preferably 90 to 180 micrograms BIW for at least four weeks, and the amount of pegylated interferon alfa-2a administered in the second treatment time period is in the range of 20 to 250 micrograms once a week(QW), preferably 90 to 180 micrograms QW for up to forty-four weeks.

When the pegylated interferon-alfa administered is a pegylated interferon alfa-2a, the induction dosing amount of pegylated interferon alfa-2a administered in first treatment time period is in the range of 20 to 250 micrograms BIW preferably 90 to 180 micrograms BIW for four to twelve weeks, and the amount of pegylated interferon alfa-2a administered in the second treatment time period is in the range of 20 to 250 micrograms once a week (QW), preferably 90 to 180 micrograms QW, for thirty-six to forty-four weeks.

When the pegylated interferon-alfa administered is a pegylated interferon alfa-2a, the induction dosing amount of pegylated interferon alfa-2a administered in first treatment time period is in the range of 20 to 250 micrograms BIW, preferably 90 to 180 micrograms BIW, for one week, followed by 20 to 200 micrograms BIW, preferably 120 to 180 micrograms BIW, for four weeks, and the amount of pegylated interferon alfa-2a administered in the second treatment time period is in the range of 20 to 250 micrograms once a week(QW), preferably 90 to 180 micrograms QW for forty-three weeks.

When the pegylated interferon-alfa administered is a pegylated interferon alfa-2a, in first treatment time period, the induction dosing amount of pegylated interferon alfa-2a administered is in the range of 20 to 250 micrograms BIW, preferably 120 to 180 micrograms BIW, for twelve weeks, and the amount of pegylated interferon alfa-2a administered in the second treatment time period is in the range of 20 to 250 micrograms per week on a weekly basis(QW), preferably 90 to 180 micrograms QW, for thirty-six weeks.

The term "pegylated interferon alfa" as used herein means polyethylene glycol modified conjugates of interferon alfa, preferably interferon alfa-2a and -2b. The preferred polyethylene-glycol-interferon alfa-2b conjugate is $PEG_{12000}$-interferon alfa 2b. The phrases "12,000 molecular weight polyethylene glycol conjugated interferon alpha" and "$PEG_{12000}$-IFN alfa" as used herein mean conjugates such as are prepared according to the methods of International Application No. WO 95/13090 and containing urethane linkages between the interferon alfa-2a or -2b amino groups and polyethylene glycol having an average molecular weight of 12000.

The preferred $PEG_{12000}$-intertferon alfa-2b is prepared by attaching a PEG polymer to the epsilon amino group of a lysine residue in the IFN alfa-2b molecule. A single $PEG_{12000}$ molecule is conjugated to free amino groups on an IFN alfa-2b molecule via a urethane linkage. This conjugate is characterized by the molecular weight of $PEG_{12000}$ attached. The PEG12000-IFN alfa-2b conjugate is formulated as a lyophilized powder for injection. The objective of conjugation of IFN alfa with PEG is to improve the delivery of the protein by significantly prolonging its plasma half-life, and thereby provide protracted activity of IFN alfa.

The term "interferon-alfa" as used herein means the family of highly homologous species-specific proteins that inhibit viral replication and cellular proliferation and modulate immune response. Typical suitable interferon-alfas include, but are not limited to, recombinant interferon alfa-2b such as Intron-A interferon available from Schering Corporation, Kenilworth, N.J., recombinant interferon alfa-2a such as Roferon interferon available from Hoffmann-La Roche, Nutley, N.J., recombinant interferon alpha-2C such as Berofor alpha 2 interferon available from Boehringer Ingelheim Pharmaceutical, Inc., Ridgefield, Conn., interferon alpha-n1, a purified blend of natural alfa interferons such as Sumiferon available from Sumitomo, Japan or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alfa-n3 a mixture of natural alfa interferons made by Interferon Sciences and available from the Purdue Frederick Co., Norwalk, Conn., under the Alferon Tradename. The use of interferon alfa-2a or alpha 2b is preferred. Since interferon alpha 2b, among all interferons, has the broadest approval throughout the world for treating chronic hepatitis C infection, it is most preferred. The manufacture of interferon alpha 2b is described in U.S. Pat. No. 4,530,901.

Other interferon alfa conjugates can be prepared by coupling an interferon alfa to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alfa-polymer conjugates are described in U.S. Pat. Nos. 4,766,106, 4,917,888, European Patent Application No. 0 236 987, European Patent Application Nos. 0510 356,0593 868 and 08098 996) pegylated interferon-alfa-2a) and International Publication No. WO 95/13090.

Pharmaceutical composition of pegylated interferon alfa-suitable for parenteral administration may be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g. human serum albumin), toxicity agents (e.g. NaCl), preservatives (e.g. thimerosol, cresol or benylalcohol), and surfactants (e.g. tween or polysorabates) in sterile water for injection. The pegylated interferon alfa-may be stored as lyophilized powders under a refrigeration at 2°–8° C. The reconstituted aqueous solutions are stable when stored between 20 and 8° C. and used within 24 hours of reconstitution. See for example U.S. Pat. Nos. 4,492,537; 5,762,923 and 5,766,582.

The term "patients having chronic hepatitis C infections" as used herein means any patient having chronic hepatitis C and includes treatment naive patients, relapsers and non-responders.

These patients having chronic hepatitis C include those who are infected with mutiple HCV genotypes including type 1 as well as those infected with, inter alia, HCV genotypes 2 2 and/or 3 as well as HCV genotypes 2, 3, 4, 5 and/or 6 and other possible HCV genotypes.

The term "treatment naive patients" as used herein means patients with chronic hepatitis C who have never been treated with ribavirin or any interferon, including but not limited to interferon-alfa, or pegylated interferon alfa.

The term "relapsers" as used herein means patients with chronic hepatitis C who have relapsed after initial response to previous treatment with interferon alone, or in combination with ribavirin.

The term "non-responders" as used herein means patients with chronic hepatitis C who have not responded to prior treatment with any interferon alone, or in combination with ribavirin.

A person suffering from chronic hepatitis C infection may exhibit one or more of the following signs or symptoms:
(a) elevated ALT,
(b) positive test for anti-HCV antibodies,
(c) presence of HCV as demonstrated by a positive test for the presence of HCV-RNA in the serum,
(d) clinical stigmata of chronic liver disease,
(e) hepatocelluar damage.

To practice the invention, the combination therapy of pegylated interferon-alfa and ribavirin is administered to the patient exhibiting one of more of the above signs or symptoms in the first and second treatment time periods in amounts sufficient to eliminate or at least alleviate one or more of the signs or symptoms.

Ribavirin is administered to the patient in association with pegylated interferon-alfa, that is, the pegylated interferon-alfa dose is administered during the same period of time that the patient receives doses of ribavirin. Pegylated interferon-alfa formulations are not effective when administered orally, so the preferred method of administering the pegylated interferon-alfa is parenterally, preferably by subcutaneous, IV, or IM, injection. Ribavirin may be administered orally in capsule or tablet form in association with the parenteral administration of pegylated interferon-alfa. Of course, other types of administration of both medicaments, as they become available are contemplated, such as by nasal spray, transdermally, by suppository, by sustained release dosage form, and by pulmonary inhalation. Any form of administration will work so long as the proper dosages are delivered without destroying the active ingredient.

The term "no detectable HCV-RNA" in the context of the present invention means that there are fewer than 100 copies of IHCV-RNA per ml of serum of the patient as measured by quantitative, multi-cycle reverse transcriptase PCR methodology. HCV-RNA is preferably measured in the present invention by the methodology described below. This methodology is referred to herein as HCV-RNA/qPCR. The lower limit of detection of HCV-RNA is 100 copies/mL.

RNA is extracted from patient serum using a guaninidium thiocyanate-phenol-chloroform mister followed by ethanol-ammonium acetate precipitation. The precipitated RNA is centrifuged and the resulting pellet is dried in a Centrivap console (Labconco, Kansas City, Mo.). The dry pellet is then resuspended in 30 microliters of an Rnasin (Promega Corp., Madison, Wis.), dithiothritol, and diethylpyrocarbonate-treated water mixture. Samples are kept at or below −20° C. (preferably below −70° C.) until RNA reverse transcription (RT) and PCR.

In order to convert the entire RNA sequence into cDNA in the RT reaction, random hexadeoxyribonucleotides (Pharmacia Biotech, Piscataway, N.J.) are used as primers for the first strand cDNA synthesis. Two aliquots of 3 microliters of resuspended sample are added to 3 microliters of 100 ng/µl random primers and denaturated at 70° C., then reverse transcribed at 40° C. for one hour using M-MLV reverse transcriptase (USB, Cleveland, Ohio) in standard buffer containing 5 mM $MgCl_2$. The final RT reaction volume is 26 µl. The PCR is started immediately following the reverse transcription.

A modified version of the PCR method is performed using heat-stable Taq polymerase to amplify the cDNA. Seventy-five microliters of PCR mix is added to the entire RT reaction volume (26 µl) to a final $MgCl_2$ concentration of 1.5 mM in a total volume of 101 µl. Each 101 µl sample is then split into 50.5 µl, and a layer of mineral oil is placed on top to prevent evaporation.

The PCR cycle consists of annealing for 90 sec., extension for 90 sec., and denaturation for 90 sec., at 55° C., 74° C. and 94° C., respectively. Thermocycling samples is submitted to a final 74° C. extension for 10 minutes. Four different cycle sets are used. By loading the sample in duplicate, and splitting these samples evenly after RT, there are four tubes from one sample. Each of the four tubes is given a different cycle number, enhancing sensitivity and accuracy in the quantitation process. The thermocycling efficiency will be assessed by satisfactory amplification of known copy number RNA standards included in each set of 60 tubes. Two primer sets are used for the amplification, both from the 5' untranslated region of the HCV genome. Both of these primer sets are highly conserved and detect all known subtypes of HCV. Primer set 1: upstream 5'-GTG GTC TGC GGA ACC GGT GAG T-3' (SEQ ID NO:1), downstream 5'-TGC ACG GTC TAC GAG ACC TC-3' (SEQ ID NO:2) which produces a 190 bp product. Primer set 2: upstream 5'-CTG TGA GGA ACT ACT GTC TTC-3' (SEQ ID NO:3), downstream 5'-CCC TAT CAG GCA GTA CCA-3' (SEQ ID NO:4) which produces a 256 bp product.

The amplified cDNA is then electrophorised in 3% agarose gel and transferred to nylon membrane. The target DNA is detected by Southern blotting and immunostaining using a nonradioactive digoxigenin-labeled DNA probe. These procedures are performed using automated instruments for PCR thermocycling, agarose gel electrophoresis, vacuum-transfer Southern blot, hybridization, and immunostaining. Each membrane contains known copy number serially diluted standards which are used to construct standard curves for quantitative measurement of the specimen bands. Originally standard curves are made from carefully diluted HCV-RNA from transcribed clones. Radioactive incorporation studies, gel electrophoresis, and OD 260 are performed on the transcripts to determine that they are of the expected length. After the production of the RNA transcripts quantitated clone standards "pooled" standards are generated which better represent the heterogeneous nature of HCV, one would encounter in natural infection. These pools are made by combining large amounts of serum or plasma from known infected individuals. The serum/plasma pools are calibrated with PCR, against the clone transcripts and then diluted in the known PCR-negative fluids. Finally, the higher copy number samples of the pools are checked against the cDNA Quantiplex nucleic acid detection system from Chiron Inc. (Emeryville, Calif.). These "double quantitated" pools are aliquoted and saved at −70° C. Dilutions of 5,000,000, 1,000,000, 500,000, 100,000, 10,000, and 1000 copies/ml are used in each experiment.

Each Southern blot membrane is scanned into a computer using an automated scanner/densitometer, at intervals during development to determine when the standard curve is most linear. The resultant electronic images are then measured for band area and mean band density. All of the reading are standardized to integrated band density and compared to the standard curve to obtain a numerical value of viral copy number for each band.

The term "sustained virologic response" as used in the context of the present invention means that there is no detectable HCV-RNA in the patients treated in accordance with the present invention for at least 24 weeks after the end of the combined therapy treatment. Preferably, the period of sustained virologic response will be at least one year—or longer—after the end of treatment. For HCV genotyping, INNO-L PA HCV (Innogenetics, Zeijmaurde, Belgium) second generation assay may be used.

The following clinical protocol may be used to administer the combination therapy of the present invention:

Overall Design and Plan of the Study

A prospective, multicenter, randomized, double-blind, parallel-group will be used. Two studies each with two treatment regimes will be used. Study No. 1 will compare treatment with pegylated Intron A, 1.5 micrograms per kilogram SC once a week (QW) in combination with ribavirin, 1000 to 1200 mg per day PO for four weeks followed by pegylated Intron A, 0.5 micrograms per kilogram SC once a week, in combination with ribavirin, 1000 to 1200 mg per day PO for forty-four weeks to treatment with pegylated Intron A, 1.5 micrograms per kilogram SC once a week in combination with ribavirin, 1000 to 1200 mg per day PO for forty-eight weeks. Study No. 2 will compare treatment of pegylated Intron A, 1.5 micrograms per kilogram SC BIW in combination with ribavirin, 1000–1200 mg/day PO for four weeks followed by pegylated INTRON A 1.5 micrograms/kilogram SC QW in combination with ribavirin, 1000–1200 mg/day PO for forty-four weeks to the treatment REBETRON Combination Therapy (Intron A, 3 MIU SC TIW in combination with ribavirin, 1000 to 1200 mg per day PO) for forty-eight weeks in patients with compensated chronic hepatitis C. Eligible patients are those 18–65 years of age, male and female subjects who should have chronic hepatitis C confirmed by positive serum HCV-RNA, liver biopsy, and laboratory tests.

Treatment group assignments should be made by a Central Randomization Center. The randomization procedure should be designed to attempt to balance the treatment groups, within and across sites, with respect to presence or absence of cirrhosis in the pretreatment liver biopsy, serum HCV-RNA/qPCR level, and HCV genotype.

During treatment and posttreatment follow-up, biochemical (ALT), virological (HCV-RNA), and histological (liver biopsy) examinations would be used to assess the nature and duration of response to study treatment. The primary efficacy variable will be the overall response defined as loss of serum HCV-RNA/qPCR (<100 copies/mL) as measured at 24 weeks following the end of therapy. In addition, a decrease in hepatic inflammation, an improvement in post-treatment liver biopsy as measured by the Knodell Histology Activity index (HAI) and normalization of ALT will also be examined as a secondary efficacy endpoints. The safety of the study treatments will be assessed by monitoring selected laboratory parameters and by also recording and evaluating the occurrence of any adverse events.

Treatment Regimens

There are two studies, each with two treatment regimens:

Study #1

1. (a) Pegylated INTRON® A 1.5 micrograms per kilogram SC once a week (QW) plus ribavirin 1000–1200 mg/Kg/day PO in two divided doses for 4 weeks; followed by (b) Pegylated INTRON® A 0.5 micrograms per kilogram SC INTRON® A once a week (QW) plus ribavirin 1000–1200 mg/Kg/day PO in two divided doses for 44 weeks.

2. (a) Pegylated INTRON® A 1.5 micrograms per kilogram once a week (QW) plus ribavirin 1000–1200 mg/Kg/day PO in two divided doses for 44 weeks.

Study #2

3 (a) Pegylated INTRON® A 1.5 micrograms per kilogram twice a week (BIW) plus ribavirin 1000–1200 mg/Kg/day PO in two divided doses for 4 weeks; followed by (b) Pegylated INTRON® A 1.5 micrograms per kilogram INTRON® A once a week (QW) plus ribavirin 1000–1200 mg/Kg/day PO in two divided doses for 44 weeks.

4. (a) INTRON® A 3 MIU SC three times a week (TIW) plus ribavirin 1000–1200 mg/Kglday PO in two divided doses for 48 weeks.

Studies No. 1 and 2 including treatments 1 and 2 and 3 and 4 should be administered for 48 weeks.

Exclusion Criteria: Patients having chronic hepatitis C who should be excluded from treatment in accordance with the present invention include, inter alia., women who are pregnant or nursing; those with suspected hypersensitivity to pegylated interferon alfa or ribavirin; those with normal ALT at screenin or entry visit, as well as those with any known pre existing condition(e.g. pre existing psychiatric condition especially severe depression or a history of severe psychiatric disorder) that in the opinion of the attending clinician would interfere with the subject's participation in and completion of the protocol.

The randomization procedure may be designed to balance the groups with respect to the following Baseline characteristics:

pretreatment liver histology (cirrhosis or no cirrhosis);

serum HCV-RNA/qPCR status (HCV-RNA/qPCR≦2,000,000 or HCV-RNA/qPCR>2,000,000 copies/mL); and HCV Genotype (1 or other). Patients with mixed genotypes (which include Type 1) will be classified as Type 1 for purposes of balancing.

Efficacy

The primary efficacy objective will be the sustained virologic response rate defined as loss of (detectable) serum HCV-RNA/qPCR measured at 24 weeks following the end of therapy to an undetectable level or to a level <100 copies/mL. The following secondary efficacy Endpoints will also be examined:

The secondary efficacy Endpoints:

proportion of patients with normalization of ALT at 24 weeks of follow-up;

proportion of patients with improvement in biopsy (Categories I+II+III combined scores);

change from Baseline in the biopsy scores (Categories I+II+III combined scores);

response rates at Endpoint of treatment based on HCV-RNA/qPCR;

proportion of patients with normalization of ALT at Endpoint of treatment.

response rates at 24 weeks of follow-up based on HCV-RNA/qPCR.

Virology: Entry Status and Change from Entry

Serum HCV-RNA/qPCR testing and genotype testing will be performed by a central laboratory. A positive HCV-RNA assay result will be required at Baseline; only patients positive for HCV-RNA will be eligible to participate. Repeat assays should be scheduled at Weeks 4, 12, 24, 36 and 48. All patients should have repeat assays scheduled for Follow-up Weeks 12 and 24.

Response will be assessed as defined below:

A patient will be classified as a sustained responder at a given time point if HCV-RNA/qPCR is negative (<100 copies per mL) at that time point.

A patient will be classified as a sustained responder if the patient is a responder at 24 weeks of follow-up.

Note that patients who do not meet these criteria, including patients who discontinued before the required HCV-RNA/qPCR evaluations are obtained, will be classified as non-responders.

Based on both serum HCV-RNA/qPCR and change in liver histology as evaluated by the Knodell HAI Inflammation Score. A patient will be classified as an overall responder to treatment if he/she is a sustained responder and his/her Post treatment Knodell HAI inflammation score (sum of categories I+II+III) improved by 2 or more units relative to the Pretreatment score.

Liver Histology

Liver biopsy will be required within the six months preceding patient enrollment and at Follow-up Week 24 for all patients. Evaluation of the biopsies will be performed by a single pathologist using the Knodell Histology Activity Score. The central pathologist will be blinded with respect to patient identification, treatment group, and the time the biopsy will be obtained relative to treatment (Pre- or Posttreatment). Efficacy of study treatments will be assessed by comparing the degree of inflammatory activity observed at Baseline with that present at Follow-up Week 24.

The patient's weight and their baseline disease characteristics (HCV genotype and initial viral load) for all patients will be measured before the start of the study. HCV genotypes should be done on the patient serum samples subjected to HCV-RNA/qPCR testing.

This enhancement of efficacy included all aspects of the disease will result in:

Sustained eradication of detectable HCV-RNA;

Improvement in hepatic inflammation;

Normalization of ALT;

Improvement in HQL.

We claim:

1. A method of treating a patient having a chronic hepatitis C infection to eradicate detectable HCV-RNA as measured by quantitative PCR ("qPCR") which comprises (1) administering to the patient in a first treatment time period of at least about four weeks up to about twelve weeks, about 400–1600 mg per day of ribavirin and about 1.5 micrograms per kilogram of pegylated interferon-alfa-2b twice a week, followed by (2) administering to the patient in a second treatment time period of about thirty-six weeks up to about forty-four weeks, about 800–1200 mg per day of ribavirin and about 0.5 to about 1.5 micrograms per kilogram of pegylated interferon-alfa-2b once a week, wherein the patient has no detectable HCV-RNA as measured by qPCR at the end of the second treatment time period and no detectable HCV-RNA as measured by qPCR for at least 24 weeks after the end of the second treatment time period.

2. The method of claim 1, wherein the amount of ribavirin administered in the first treatment time period is from 600 to 1600 mg per day.

3. The method of claim 1, wherein the amount of ribavirin administered in the second treatment time period is from 1000 to 1600 mg per day.

4. The method of claim 1, wherein the first treatment time period is four weeks and the second period is forty-four weeks.

5. The method of claim 1, wherein the amount of pegylated interferon alfa-2b administered in second treatment time period is 1.5 micrograms/kilogram once a week.

6. The method of claim 1, wherein the amount of ribavirin administered in the first and second treatment time periods is from about 800 to 1200 mg per day.

7. The method of claim 1 wherein the amount of ribavirin administered in the first and second treatment time period is about 1000 to 1200 mg/kg per day.

8. A method of treating a patient having a chronic hepatitis C infection to eradicate detectable HCV-RNA as measured by qPCR which comprises (1) administering to the patient, in a first treatment time period week of about four weeks, about 400–1600 mg per day of ribavirin and 1.5 micrograms per kilogram of pegylated interferon-alfa-2b twice a week, followed by (2) administering to the patient, in a second treatment time period of about forty-four weeks, about 800–1200 mg per day of ribavirin and about 0.5 to 1.5 micrograms per kilogram of pegylated interferon-alfa-2b once a week wherein the patient has no detectable HCV-RNA as measured by qPCR at the end of the second treatment time period and no detectable HCV-RNA as measured by qPCR for at least 24 weeks after the end of the second treatment time period.

9. The method of claim 8, wherein the amount of ribavirin administered in the first treatment time period is from 600 to 1600 mg per day.

10. The method of claim 8, wherein the amount of ribavirin administered in the second treatment time period is from 1000 to 1600 mg per day.

11. The method of claim 8, wherein the amount of ribavirin administered in the first and second treatment time periods is from about 800 to 1200 mg per day.

12. The method of claim 8 wherein the patient having chronic hepatitis C infection is a treatment naive patient having HCV genotype 1, 2 or 3.

13. The method of claim 8, wherein the amount of pegylated interferon alfa-2b administered in second time period is 1.5 micrograms/kilogram once a week.

14. The method of claim 8, wherein the amount of pegylated interferon alfa-2b administered in second time period is 1.0 micrograms/kilogram once a week.

15. The method of claim 8, wherein the amount of pegylated interferon alfa-2b administered in second time period is 0.5 micrograms/kilogram once a week.

* * * * *